US006462071B1

(12) United States Patent
Castillejos

(10) Patent No.: US 6,462,071 B1
(45) Date of Patent: Oct. 8, 2002

(54) AGENTS FOR INTRAVITREAL ADMINISTRATION TO TREAT OR PREVENT DISORDERS OF THE EYE

(75) Inventor: David Castillejos, Chula Vista, CA (US)

(73) Assignee: Vitreo-Retinal Technologies, Inc., Irvine, CA (US)

( * ) Notice: Subject to any disclaimer, the term of this patent is extended or adjusted under 35 U.S.C. 154(b) by 0 days.

(21) Appl. No.: 09/517,798

(22) Filed: Mar. 2, 2000

(51) Int. Cl.[7] .......................... A61K 31/40; A61K 31/17
(52) U.S. Cl. .................. 514/413; 514/588; 514/912
(58) Field of Search ................... 514/588, 413, 514/912

(56) References Cited

U.S. PATENT DOCUMENTS

| 5,110,493 A | 5/1992 | Cherng-Chyi et al. |
| 5,441,984 A | 8/1995 | Heath, Jr. et al. |
| 5,554,187 A | 9/1996 | Rizzo, III |
| 5,629,344 A | * 5/1997 | Charlton et al. ............ 514/588 |
| 5,891,084 A | 4/1999 | Lee |
| 5,891,913 A | 4/1999 | Sallmann et al. |

\* cited by examiner

*Primary Examiner*—Zohreh Fay
(74) *Attorney, Agent, or Firm*—Robert D. Buyan; Stout, Uxa, Buyan & Mullins, LLP

(57) ABSTRACT

Methods and preparations for treating disorders of the eye and/or causing posterior vitreous disconnection or disinsertion. Preparations containing a) urea, b) urea derivatives (e.g., hydroxyurea, thiourea), c) a non-steroidal anti-inflamatory agents, d) antmetabolites, e) urea, urea derivatives, non-enzymatic proteins, nucleosides, nucleotides and their derivatives (e.g., adenine, adenosine, cytosine, cytadine, guanine, guanitadine, guanidinium, thymidine, thimitadine, uradine, uracil, cystine), uric acid, calcium acetal salicylate, ammonium sulfate or other compound capable of causing non-enzymatic dissolution of the hyaloid membrane or e) any of the possible combinations thereof, are administered to the eye in therapeutically effective amounts.

15 Claims, No Drawings

AGENTS FOR INTRAVITREAL ADMINISTRATION TO TREAT OR PREVENT DISORDERS OF THE EYE

FIELD OF THE INVENTION

The present invention relates generally to pharmaceutical preparations and medical treatment methods, and more particularly agents (i.e, urea and urea derivatives, nonsteroidal anti-inflammatory drugs (NSAIDS) and antimetabolite drugs) used alone or in combinations with each other (or with other agents) to treat or prevent certain disorders of the eye.

BACKGROUND OF THE INVENTION

A. Neovascularization

Neovascularization (or angiogenesis) is a process whereby new blood vessels are formed within tissues of the body. Normal neovascularization is the physiological process by which the body creates and maintains small blood vessels of the circulatory system. However, pathological or iatrogenic neovascularization is a non-physiological process whereby abnormal networks of blood vessels are created in tissues of the body or in tumors, as a result of certain diseases, trauma or surgical procedures.

Pathologcal neovasclarization occurs within tissues of the eye as a result of certain ophrbalmic disorders such as diabetic retinoparbies, proliferatve vitreo-retinopathies, corneal neovascularization, iris rubeosis, and diseases that cause isctiemia of the ocalar tissues (e.g., occlusion of the central retinal vein, occlsion of the central retinal artery, certain inflammatory corldilions, etc.). Also, iatrogenic neovasculdriation can occur following certain ophthalmological surgical procedures which disrupt normal blood supply to tissues of the eye or those which cause localized proliferations of cells known as "fibroblasts". Examples of ophthalmological surgical procedures that have been associated with untoward post-surgical neovascularization include glaucoma filtration surgery and corneal transplant surgery.

Various types of drugs and agents (e.g., steroids, non-steroidal anti-inflammatory drugs (NSAIDS), heparin, protamine, calcitrol, antibiotics, thrombospodin fragments, and monoclonal antibodies directed to fibroblast growth factor) have been purported to be useable to treat or prevent neovascularization of the anterior segment of the eye. Non steriodal anti-inflammatory drugs have not been used to treat neovascularization of the posterior segment of the eye.

Also, laser surgical procedures have been used to ablate or destroy neo-vascular networks which develop in the retina or epiretinal membranes. However, these prior therapies for ocular neovascularization have been less than completely effective and/or have been associated with side effects. For example, glucocorticoids and other angiostatic steroids have been used to treat neovascularization of the anterior chamber (e.g., corneal neovascularization, iris rubeosis) and/or other ocular tissues, but such steroid treatments have been associated with side effects such as elevated intraoccular pressure. see, Kitazawa, *Increased Intraocular Pressure Induced by Corticosteroids*, American Journal of Ophthalmology, Vol. 82, Pg.492–493 (1976)

B. Intravitreal Hemorrhage and the Need for Liquefaction of the Vitreous Body and/or Posterior Vitreous Dissinsertion or Detachment Prior to Vitrectomy In many mammals including human beings, the "vitreous body" is disposed within a posterior portion of the eye and occupies approximately four fifths of the cavity of the eyeball, behind the lens. The vitreous body is formed of gelatinous material, known as the vitreous humor. The vitreous humor of a normal human eye is made up of approximately 99% water along with 1% macromolecules including; collagen, hyaluronic acid, soluble glycoproteins, sugars and other low molecular weight metabolites.

The retina is essentially a layer of nervous tissue which covers a portion of the inner wall of the posterior segment—in juxtaposition to the posterior aspect of the vitreous body. The retina is surrounded by a layer of cells known as the choroid layer. The retina may be divided into a) an optic portion which participates in the visual mechanism, and b) a non-optic portion which does not participate in the visual mechanism. The optic portion of the retina contains the rods and cones, which are the effectual organs of vision. A number of arteries and veins enter the retina at its center, and splay outwardly to provide blood circulation to the retina.

The posterior portion of the vitreous body is in direct contact with the retina. Networks of fibrillar strands extend from the retina and permeate or insert into the vitreous body so as to attach the vitreous body to the retina.

Diabetic retinopathy, trauma and other ophthalmological disorders sometimes result in rupture or leakage of retinal blood vessels with resultant bleeding into the vitreous humor of the eye (i.e., "intravitreal hemorrhage). Such intravitreal hemorrhage typically manifests as clouding or opacification of the vitreous humor.

Intravitreal hemorrhage is sometimes, but not always, accompanied by tearing or detachment of the retina. In cases where the intravitreal hemorrhage is accompanied by a retinal tear or detachment, it is important that such retinal tear or detachment be promptly diagnosed and surgically repaired. Failure to promptly diagnose and repair the retinal tear or detachment may allow photo-receptor cells of the retina, in the region of the tear or detachment, to become necrotic. Such necrosis of the photoreceptor cells of the retina may result in loss of vision. Furthermore, allowing the retinal detachment to remain unrepaired for such extended period of time may result in further intravitreal hemorrhage and/or the formation of fibrous tissue at the site of the hemorrhage. Such formation of fibrous tissue may result in the formation of an undesirable fibrous attachment between the vitreous body and the retina.

The typical surgical procedure used for repair of retinal tears or detachment requires that the surgeon be able to look through the vitreous humor, to visualize the damaged region of the retina (i.e., "transvitreous viewing of the retina"). When intravitreal hemorrhage has occurred, the presence of the hemorrhagic blood within the vitreous can cause the vitreous to become so cloudy that the surgeon is prevented from visualizing the retina through the vitreous. Such hemorrhagic clouding of the vitreous can take 6–12 months or longer to clear sufficiently to permit trans-vitreal viewing of the retina. However, in view of the potential complications which may result from delayed diagnosis or treatment of a retinal tear or detachment, it is generally not desirable to wait for such natural clearance of the hemorrhagic blood to occur.

Furthermore, even when the intravitreal hemorrhage is not accompanied by retinal tear or detachment, it is often difficult to verify that retinal tear or detachment has not occurred, because the hemorrhagic clouding of the vitreous prevents the physician from performing routine funduscopic examination of the retina. Moreover, the presence of hemorrhagic blood within the vitreous may significantly impair the patient's vision through the affected eye, and will continue to do so until such time as the hemorrhagic blood has been substantially or fully cleared.

Thus, the presence of hemorrhagic blood within the vitreous body causes multiple clinical problems including a) inability to visually examine and diagnose the site of the hemorrhage and/or any accompanying tear or detachment of the retina, b) full or partial impairment of vision in the affected eye and c) impairment or prevention of the performance of trans-vitreal surgical procedures of the type typically utilized to repair the site of hemorrhage and/or to repair any accompanying retinal tear or detachment. In cases where intravitreal hemorrhage has resulted in substantial clouding or opacification of the vitreous, the treating physician may have the option to perform a procedure known as a vitrectomy, wherein all (or a portion of) the vitreous body is removed from the interior of the eye, and replaced with a clear liquid or gas. The performance of such vitrectomy procedure is intended to allow the surgeon to visualize the retina sufficiently to proceed with the necessary retinal examination and/or surgical repair of the hemorrhage and any accompanying retinal tear or detachment. However, such vitrectomy procedures are highly skill-intensive, and are associated with several significant drawbacks, risks and complications. Among these drawbacks, risks and complications are the potential that the act of removing the vitreous will cause further detachment or tearing of the retina and/or that such removal of the vitreous will cause further hemorrhage from the already-weakened retinal blood vessels. In order to minimize the stress of tugging on the retina during vitrectomy and to otherwise facilitate the removal of the vitreous body, it is sometimes desirable to precede the vitrectomy by the intravitreal injection of a substance which will cause liquefaction of the vitreous humor and/or disinsertion/detachment of the vitreous humor from the adjacent tissues of the retina and epiretinal membranes. Examples of substances which have been purported to cause vitreal liquefaction and/or posterior vitreous detachment/disinsertion are found in U.S. Pat. No. 4,820,516 (Sawyer), U.S. Pat. No. 5,292,509 (Hageman) and U.S. Pat. No. 5,866,120 (Karageozian et al.).

C. Prior Ophthalmic Applications of Urea and Urea Derivatives

U.S. Pat. No. 5,629,344 (Charlton et al.) has described the topical application to the cornea or "surface" of the eye of urea and/or urea derivative(s) to treat ocular conditions such as dryness, non-infectious keratitis, irregularities of the corneal or conjunctival epithelium, ocular scarring and "subjective irritations" as well as to inhibit unwanted fibroblast formation and/or enhance healing following glaucoma, cataract and corneal surgeries.

D. Prior Ophthalmic Applications of Non-Steroidal Anti-Inflammatory Agents

Several NSAIDS have heretofore been known for oral administration and/or topical application to the eye for the purpose of treating inflammatory conditions of the eye and/or post surgical pain and inflamation of the anterior segment of the eye. Examples of NSAIDS that are presently available for topical application to the eye include diclofenac (Cataflam), flurbiprofen (Ansaid), ketorolac (Toradol, Acular). To date, ophthalmic NSAID preparations have been used primarily to treat inflammatory disorders of the comea and anterior segment of the eye. In instances where ophthalmic NSAIDS have been administered to treat disorders of the posterior segment of the eye, the NSAID has been initially applied to the anterior segment of the eye with the intention that a therapeutic amount of the NSAID will distribute from the anterior segment to the posterior segment of the eye where the therapeutic effect is desired. For example, Acular™ (ketorolac) drops have been applied topically to the anterior segment of the eye (i.e., to the cornea) for the purpose of treating cystoid macular edema—a disorder of the posterior segment of the eye.

E. Prior Ophthalmic Applications of Anti-Metabolites

5-Fluorouracil and Mitomicin C have previously been purported to be useable, when administered to the anterior segment of the eye, to inhibit or treat certain conditions of the anterior segment that are characterized by undesired tissue proliferation such as benign fibrovascular lesions of the conjunctiva known as Pterygia.

SUMMARY OF THE INVENTION

The method of the present invention is carried out for the purpose of bringing about one or more of the following effects;

causing non-enzymatic dissolution of the hyaloid interface (i.e.,hyaloid membrane) or other proteins or amino acids responsible for maintaining attachment between the vitreous body and retina of a mammalian eye, or otherwise inducing posterior vitreous detachment and/or disinsertion of the vitreous body from the retina and epiretinal membranes (hereinafter referred to as "PVD");

causing liquefaction of the vitreous humor;

causing diffusion or preventing the accumulation of localized concentrations near the retina of substances that are injurious or pathogenic to the retina (e.g., angiogenic factors);

causing dissolution of coagulum within the vitreous humor (as may occur following intravitreal hemorrhage);

causing a solvent action on fibroblasts;

inhibiting fibroblasts inhibiting or preventing fibrosis associated with the presence of vitreous heme;

inhibiting the proliferation of fibroblasts in ocular tissues; and, causing reactivation (e.g., regeneration, regrowth, stimulation, up-regulation or improved neuronal transmission) of inactive nerves or nerve fibers (e.g., optic nerve).

By one or more of the above-listed effects, or by other mechanisms, the method of the present invention is useable for various therapeutic and/or prophylactic applications, including but not limited to:

treating (e.g., as used herein "treating" shall mean preventing, deterring, stopping, curing or slowing the progression of) diabetic retinopathy;

treating intravitreal hemorrhage and accelerating the clearance of hemorrhagic blood from the vitreous humor;

inducing PVD and/or liquefaction of the vitreous prior to the performance of a vitrectomy thereby limiting the likelihood of retinal detachment, retinal tearing, re-stimulation of retinal hemorrhage or other complications of the vitrectomy procedure;

treating vitreous traction associated with macular holes;

treating macular degeneration;

treat retinitis pigmentosa;

prophylaxis to retinal detachment in patients who are at high risk for retinal detachment (e.g., high myopes);

treating preretinal and subretinal membranes;

treating cystoid macular edema;

pre-operative preparation of the eye in the surgical treatment of eye trauma;

pre-operative treatment prior to certain types of glaucoma surgery (e.g., those performed for the treatment of neovascular glaucoma);

treating occlusion of the central retinal vein or central retinal artery;

treating conditions associated with neovascularization such as neovascular iris and neovascular glaucoma;

treating ocular ischemic syndrome;

treating conditions associated with posterior eye inflamation such as VKH, pars planitis, toxoplasmosis, etc.; and, improving the delivery and bioavilability to the retina and other tissues of intravitreally administered drugs;

treating pterygia (e.g., loxopterygium, pimelopterygium, symblepharopterygium);

treating stromal-corneal neovascularization;

treating glaucoma blebs;

treating optic nerve atrophy or impaired optic nerve activity of any cause; and, treating glaucoma-induced cupping of the optic nerve.

Further in accordance with the invention, the urea and urea derivative agents useable in the method comprise urea, hydroxyurea and thiourea.

Still further in accordance with the invention, the agents of the present invention may be administered by injection into the eye (e.g., intravitreal, intrastromal or subconjunctival injection).

Still further in accordance with the invention, the non-steroidal anti-inflammatory drugs that are most suitable for use in the method of the present invention include the heteroaryl acetic acids (e.g., tolmetin, diclofenac, ketorolac) and the arylpropionic acids (e.g., ibuprofen, naproxen, flurbiprofen, ketoprofen, fenoprofen, oxaprozin). Combination of an NSAID with urea or a urea-containing compound is particularly useable for the treatment of posterior inflammatory conditions such as VKH, pars planitis, toxoplasmosis, etc.

Still further in accordance with the invention, the antimetabolite compounds that are useable in the method comprise, mitomicyn C, methotrexate, thiourea, hydroxyurea, 6-mercaptopurine, thioguanine, 5-fluorouracil, cytosine arabinoside and 5-azacytidine. (Thiourea and hydroxyurea are anti-metabolites as well as urea derivatives.) Other anti-neoplastic compound such as Actinomycin D, daunorubicin, doxorubicin, idarubicin, bleomycins, or plicamycin may also be used in combination with these anti-metabolites. Combinations of these antimetabolite agents (or other anti-neoplastic drugs) with urea or a urea-containing compounds are particularly useable for the treatment of Intraocular tumors, posterior uveitis, wet macular degeneration, age related macular degeneration (dry form), retinitis pigmentosa, retina of prematurity (ROP), retinal vasculitis (e.g., secondary to Eales disease, lupus retinopathy, sarcoidosis, etc.), neovascular glaucoma, phacomorphic reactions and sympathetic ophthalmia.

Still further in accordance with the invention, PVD may be induced by the administration (e.g. intravitreal injection) of therapeutically effective amotint(s) of one or more agents that cause non-enzyrnaric dissolution of the hyaloid membrane or hyaloid interface. As a result of such hyaloid dissolution, the vitreous body will become detached or disinserted from the retina, thereby allowing vitrectomy, repair of retinal tears, or other procedure to be performed with lessened chance for inducing retinal rearing or retinal hemorrhage. For example, in may traditional vitrectomy procedures, the tugging or cutting away of the vitreous body can result in tearing or damage to the retina because the hyaloid interface remains intact. Also, after the vitreous body has been substantially removed using a vitrectomy cutter, the physician must (in many cases) peel the remaining hyaloid membrane away from the retina. Such peeling away of the hyaloid from the retina can further cause retinal tearing or damage. Thus, by administering one or more compounds capable of causing non-enzymatic dissolution of the hyaloid membrane, PVD may be induced and such potential for iatrogenic damage to the retina will be minimized. Examples of agents that may be administered by intravitreal injection to cause such non-enzymatic dissolution of the hyaloid membrane include urea, urea derivatives, urea, urea derivatives, non-enzymatic proteins, nucleosides, nucleotides and their derivatives (e.g., adenine, adenosine, cytosine, cyradine, guanine, guanitadine, guanidinium, thymidine, thimitadine, uradine, uracil, cystine), uric acid, calcium acetal salicylate and ammonium sulfate.

Still further aspects, objects and advantages of the invention will be apparent to those of skill in the art who read and understand the following detailed description of the invention and the specific examples set forth therein.

DETAILED DESCRIPTION OF THE INVENTION

As summarized hereabove, the present invention provides urea containing solutions (i.e., solutions which contain urea, a urea derivative (e.g., hydroxyurea) and/or mixtures thereof) that are injectable into the eye alone, non-steroidal anti-inflammatory drugs (NSAIDS) injected into the eye alone and anti-metaboilities that are injected into the eye alone. Additionally, the some of the urea-containing or injectable solutions of the present invention may further contain non-steroidal anti-inflammatory agent(s) (e.g., flurbiprofen, diclofenac, ketorolac) and/or antimetabolite(s) (e.g., mitomicyn C, methotrexate, 6-mercaptopurine, thioguanine, 5-fluorouracil, cytosine arabinoside and 5-azacytidine).

Solutions of urea or hydroxyurea, which have been adjusted to a pH of approximately 4.0 to 7.0, are substantially non-toxic and well tolerated when injected intravitrially, sub-conjunctively or intrastromally, one (1), two (2) or more times, in an injectate volume of 50–100 microliters per injection, at doses of 33–5000 micrograms of urea per injection.

A. Urea Formulations

The following are examples of urea-containing solutions that are useable in accordance with this invention:

EXAMPLE 1

| | |
|---|---|
| Urea USP/NF | 4.0% |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid 0.1 N Sodium Hydroxide)

EXAMPLE 2

| | |
|---|---|
| Urea USP/NF | 4.0% |
| Citric Acid USP/NF | 0.00007–0.02% |
| Sterile Water for Injection USP | Q.S. 100% |
| pH of solution | 5.0–7.0 |

(Adjust pH using 0.1 N Hydrochloric acid 0.1 N Sodium Hydroxide)

EXAMPLE 3

| | |
|---|---|
| Urea USP/NF | 0.01%–15.0% |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 4

| | |
|---|---|
| Urea USP/NF | 4.0% |
| Potassium Phosphate Dibasic USP/NF | 5.0 millimolar |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 5

| | |
|---|---|
| Urea USP/NF | 4.0% |
| Potassium Phosphate Dibasic USP/NF | 50.0 millimolar |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 6 (Lyophilized Powder)

| | |
|---|---|
| Urea USP/NF | 0.01%–15.0% |
| Sorbitol USP/NF | 0.10%–0.50% |
| Citric Acid USP/NF | 0.00007–0.02% |
| pH of final solution | 5.0–7.0 |

(Adjust pH using 0.1 N Hydrochloric acid/0.1 N Sodium Hydroxide)

EXAMPLE 7

| | |
|---|---|
| Urea USP/NF | 4.0% |
| Sorbitol USP/NF | 0.10% |
| Citric Acid USP/NF | 0.00007–0.02% |
| pH of final solution | 5.0–7.0 |

(Adjust pH using 0.1 N Hydrochloric acid/0.1 N Sodium Hydroxide)

Citrate or phosphate buffers may alternatively be used in the above-listed formulations of Examples 1–7. Also, sodium chloride and dextrose are alternative bulking agents that could be used in the lyophilized formulation of Example 6.

B. Urea-Enzyme Solutions

The following are examples of formulations wherein urea is combined with another agent, such as an enzyme.

EXAMPLE 8

| | |
|---|---|
| Urea USP/NF | 4.0% |
| Hyaluronidase | 1.0 IU–100 IU |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid 0.1 N Sodium Hydroxide)

EXAMPLE 9

| | |
|---|---|
| Urea USP/NF | 0.01%–15.0% |
| Hyaluronidase | 1.0 IU–100 IU |
| Sodium Chloride USP/NF | up to 0.9% |
| Sterile Water for Injection USP | Q.S 100% |
| pH of solution | 5.0–7.0 |

(Adjust pH using 0.1 N Hydrochloric acid/0.1 N Sodium Hydroxide)

EXAMPLE 10

| | |
|---|---|
| Urea USP/NF | 0.01%–15.0% |
| Urokinase | 1.0 IU–50 IU |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 11

| | |
|---|---|
| Urea USP/NF | 0.01%–15.0% |
| Chondroitinase A B C | 1.0 IU–30 IU |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid 0.1 N Sodium Hydroxide)

EXAMPLE 12

| | |
|---|---|
| Hydroxy Urea | 0.01%–15.0% |
| Hyaluronidase | 1.0 IU–100 IU |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid/0.1 N Sodium Hydroxide)

C. Hydroxy Urea Solutions

The following are examples of hydroxy urea-containing formulations useable in accordance with the present invention.

EXAMPLE 13

| | |
|---|---|
| Hydroxy Urea | 4.0% |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 14

| | |
|---|---|
| Hydroxy Urea | 4.0% |
| Citric Acid USP/NF | 0.00007–0.02% |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 15

| | |
|---|---|
| Hydroxy Urea | 0.01%–15.0% |
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid/0.1 N Sodium Hydroxide)

EXAMPLE 16

| | |
|---|---|
| Hydroxy Urea | 4.0% |
| Potassium Phosphate Dibasic USP/NF | 5.0 millimolar |
| Sterile Water for Injection USP | Q.S. 100% |
| pH of solution | 5.0–7.0 |

(Adjust pH using 0.1 N Hydrochloric acid 0.1 N Sodium Hydroxide)

EXAMPLE 17

| | |
|---|---|
| Hydroxy Urea | 4.0% |
| Potassium Phosphate Dibasic USP/NF | 50.0 millimolar |
| Sterile Water for Injection USP | Q.S. 100% |
| pH of solution | 5.0–7.0 |

(Adjust pH using 0.1 N Hydrochloric acid 0.1 N Sodium Hydroxide)

EXAMPLE 18 (Lyophilized Powder)

| | |
|---|---|
| Hydroxy Urea | 0.01%–15.0% |
| Sorbitol USP/NF | 0.10%–0.50% |
| Citric Acid USP/NF | 0.00007–0.02% |
| pH of final solution | 5.0–7.0 |

(Adjust pH using 0.1 N Hydrochloric acid 0.1 N Sodium Hydroxide)

EXAMPLE 19

| | |
|---|---|
| Hydroxy Urea | 4.0% |
| Sorbitol USP/NF | 0.10% |
| Citric Acid USP/NF | 0.00007–0.02% |
| pH of final solution | 5.0–7.0 |

(Adjust pH using 0.1 N Hydrochloric acid 0.1 N Sodium Hydroxide)

D. Urea-NSAID and Hydroxy Urea-NSAID Solutions

The following are examples of formulations for Urea-NSAID and Hydroxy Urea-NSAID Solutions that are useable in accordance with the present invention.

EXAMPLE 20

| | |
|---|---|
| Flurbiprofen Sodium | 0.03% |
| Sodium Chloride USP/NF | 0.70% |
| Citrate buffer | 5.0–50.0 millimolar |
| Sterile Water for Injection USP | Q.S. 100% |
| pH of soiution | 4.0–6.0 |

(Adjust pH using 0.1 N Hydrochloric acid 0.1 N Sodium Hydroxide)

EXAMPLE 21

| | |
|---|---|
| Flurbiprofen Sodium | 0.03% |
| Urea USPNF | 4.0% |
| Citrate buffer | 5.0–50.0 millimolar |
| Sterile Water for Injection USP | Q.S. 100% |
| pH of solution | 4.0–6.0 |

(Adjust pH using 0.1 N Hydrochloric acid/0.1 N Sodium Hydroxide)

EXAMPLE 22

| | |
|---|---|
| Flurbiprofen Sodium | 0.03% |
| Hydroxy Urea | 4.0% |
| Citrate buffer | 5.0–50.0 millimolar |
| Sterile Water for Injection USP | Q.S. 100% |
| pH of solution | 4.0–6.0 |

(Adjust pH using 0.1 N Hydrochloric acid/0.1 N Sodium Hydroxide)

EXAMPLE 23

| | |
|---|---|
| Flurbiprofen Sodium | 0.01%–0.03% |
| Urea USP/NF | 0.01%–15.0% |
| Citrate buffer | 5.0–50.0 millimolar |
| Sterile Water for injection USP | Q.S. 100% |
| pH of solution | 4.0–6.0 |

(Adjust pH using 0.1 N Hydrochloric acid/0.1 N Sodium Hydroxide)

EXAMPLE 24

| | |
|---|---|
| Flurbiprofen Sodium | 0.01%–0.03% |
| Hydroxy Urea | 0.01%–15.0% |
| Citrate buffer | 5.0–50.0 millimolar |
| Sterile Water for Injection USP | Q.S. 100% |
| pH of solution | 4.0–6.0 |

(Adjust pH using 0.1 N Hydrochloric acid/0.1 N Sodium Hydroxide)

It will be appreciated that any of the above-set-forth solutions may be injected intravitreously or may be injected into other portions of the eye, to effect the therapeutic treatment(s) of the present invention.

E. Antimetabolite Formulations

The following are examples of formulations for antimetabolite solutions that are useable in accordance with the present invention.

EXAMPLE 25

| | |
|---|---|
| Hydroxyurea | 0.01%–15.0% |
| NaCl USP/NF | up to 0.9% |
| Sterile Water for Injection USP | Q.S. 100% |
| pH | 5.0–7.0 |

(Adjust pH using 0.1 N Hydrochloric acid 0.1 N Sodium Hydroxide)

EXAMPLE 26

| | |
|---|---|
| Mitomycin C | 200 μg–200 mg |
| NaCl USP/NF | up to 0.9% |
| Sterile Water for Injection | Q.S. 100% |
| pH | 5.5–7.5 |

(Adjust pH using 0.1 N Hydrochloric acid 0.1 N Sodium Hydroxide)

(Refrigerate after compounding, stable for up to 3 days)

EXAMPLE 27

| | |
|---|---|
| Mitomycin C | 200 μg–200 mg |
| Sorbital USP/NF | 0.1–0.5% |
| NaCl | 0.2% |

(lyophilized powder)

EXAMPLE 28

| | |
|---|---|
| Thiourea | 0.01%–10.0% |
| NaCl USP/NF | up to 0.9% |
| Sterile Water for Injection | Q.S. 100% |
| pH | 4.0–6.0 |

(Adjust pH using 0.1 N Hydrochloric acid 0.1 N Sodium Hydroxide)

F. NSAID Formulations

The following are examples of formulations for NSAID solutions that are useable in accordance with the present invention.

EXAMPLE 29

| | |
|---|---|
| Flurbiprofen Sodium | 0.03% |
| NaCl USP/NF | up to 0.9% |
| Citrate buffer | 5 millimoles–50 millimmoles |
| Sterile Water for Injection USP | Q.S. 100% |
| pH | 4.0–6.0 |

(Adjust pH using 0.1 N Hydrochloric acid 0.1 N Sodium Hydroxide)

EXAMPLE 30

| | |
|---|---|
| Flubiprofen | 0.01%–0.5% |
| NaCl USP/NF | up to 0.9% |
| Citrate buffer | 5 millimoles–50 millimmoles |
| Sterile Water for Injection USP | Q.S. 100% |
| pH | 4.0–6.0 |

(Adjust pH using 0.1 N Hydrochloric acid 0.1 N Sodium Hydroxide)

EXAMPLE 31

| | |
|---|---|
| Ibuprofen | 0.01%–0.5% |
| NaCl | 0.7% |
| Citrate buffer | 5 miliimoles–50 millimmoles |
| Sterile Water for Injection USP | Q.S. 100% |
| pH | 4.0–6.0 |

(Adjust pH using 0.1 N Hydrochloric acid 0.1 N Sodium Hydroxide)

EXAMPLE 32

| Ketolorac | 0.01%–0.5% |
|---|---|
| NaCl | 0.7% |
| Citrate buffer | 5 millimoles–50 millimmoles |
| Sterile Water for Injection USP | Q.S. 100% |
| pH | 4.0–6.0 |

(Adjust pH using 0.1 N Hydrochloric acid 0.1 N Sodium Hydroxide)

G. Other Agents for Non-Enzymatic Dissolution of Hyaloid Interface

As summarized hereabove, any of the above formulations containing urea or a urea derivative may be administered by intravitreal injection or otherwise caused to distribute into the vitreous or posterior segment of the eye in therapeutic concentrations, to cause non-enzymatic dissolution of the hyaloid membrane, thereby inducing PVD. As an alternative to, or in combination with, urea or a urea derivative, these formulations may contain other compounds capable of causing non-enzymatic dissolution of the hyaloid membrane such as non-enzymatic proteins, nucleosides, nucleotides and their derivatives (e.g., adenine, adenosine, cytosine, cytadine, guanine, guanitadine, guanidinium, guanidinium, thymidine, thimitadine, uradine, uracil, cystine), uric acid, calcium acetal salicylate and ammonium sulfate. For example, a guanidinium preparation of the following formulation may be administered by intravitreal injection, to deliver a dose of approximately 30micrograms to 5 milligrams, and preferably about 2 mg. The injectate volume in which each such intravitreal dose is delivered is preferably about 50 microliters per injection. As a result of one or more intravitreal injections of this guanidinium preparation, the hyaline membrane will be substantially dissolved resulting in substantial PVD.

EXAMPLE 33

| Guanidinium HCL | 0.01%–15.0% |
|---|---|
| Sodium Chloride USP/NF | up to 0.9% |
| Sterile Water for Injection USP | Q.S. 100% |
| pH of solution | 5.0–7.0 |

(Adjust pH using 0.1 N Hydrochloric acid 0.1 N Sodium Hydroxide)

It is to be appreciated that the invention has been described hereabove with reference to certain presently preferred embodiments and examples only, and no effort has been made to exhaustively describe all possible embodiments and examples wherein urea containing solutions (e.g. urea or hydroxy urea solutions) and/or solutions containing compounds capable of inducing non-enzymatic dissolution of the hyaloid membrane are used in accordance with the present invention. It is intended that all possible embodiments and examples of such solutions and the above-stated uses thereof, be included within the scope of following claims.

What is claimed is:

1. A method for treating a disorder of the eye for a purpose selected from the group consisting of;
   inducing posterior vitreous detachment and/or disinsertion of the vitreous body from the retina and epiretinal membranes;
   calling non-enzymatic dissolution of the hyaloid membrane;
   causing liquefaction of the vitreous humor;
   causing diffusion or preventing the accumulation of localized concentrations near the retina of substances that are injurious or pathogenic to the retina,
   causing dissolution of coagulum within the vitreous humor;
   treating diabetic retnopathy;
   treating intravitreal hemorrhage and accelerating the clearance of hemorrhagic blood from the vitreous humor;
   treating vitreous traction associated with macular holes;
   treating macular degeneration;
   treat retinitis pigmentosa;
   prophylaexis to retinal detachment in patients who are at high risk for retinal detachment;
   treating preretinal and subretinal membranes;
   improving the delivery to the retina and preretinal tissues of intravitreally administered drugs; and,
   as an adjunct to a vitrectomy procedure, the method comprising the step of
      (A) injecting intravitreally a therapeutically effective amount of a compound comprising urea.

2. A method according to claim 1 wherein the compound is urea.

3. A method according to claim 1 wherein the compound is a urea derivative.

4. A method according to claim 1 wherein the compound is selected from the group consisting of:
   urea;
   hydroxyurea;
   thiourea; and,
   combinations thereof.

5. A method according to claim 1 wherein the disorder of the eye is a disorder that may benefit from liquefaction of the vitreous humor and wherein the therapeutically effective amount of the compound causes vitreal liquefaction when injected intravitreally.

6. A method according to claim 1, wherein Step A comprises intravitreally injecting a solution that contains from about 30 $\mu$g to about 7500 $\mu$g urea per 50 $\mu$l to 100 $\mu$l of solution.

7. A method according to claim 6 wherein the solution delivered in Step A comprises approximately 300 $\mu$g of urea per 50 $\mu$l of solution.

8. A method according to claim 1 wherein Step A comprises intravitreally injecting a therapeutically effective amount of a solution comprising i) urea or a urea derivative in combination with ii) at least one non-steroidal anti-inflammatory agent.

9. A method according to claim 8 wherein the non-steroidal anti-inflammatory agent is selected from the group consisting of:
   flurbiprofen;
   diclofenac;
   ketorolac; and,
   combinations thereof.

10. A method according to claim 1 wherein Step A comprises intravitreally injecting a therapeutically effective amount of a solution comprising i) urea or a urea derivative in combination with ii) at least one antimetabolite.

11. A method according to claim 10 wherein the antimetabolite is selected from the group consisting of:

mitomicyn C;
methotrexate;
6-mercaptopurine;
thioguanine;
5-fluorouracil;
cytosine arabinoside;
5-azacytidine;
hydroxyurea;
thiourea; and,
combinations thereof.

12. A method according to claim 1 wherein the agent delivered in Step A comprises 2000 micrograms of urea and either 2000 micrograms of antimetabolite hydroxyurea, or 5.0 microgram of mitomicin C, per 50 microliters of solution.

13. A method according to claim 1 wherein Step A comprises intravitreally injecting approximately 300 micrograms of urea in combination with approximately 2000 micrograms of hydroxyurea per 50 microliters of solution.

14. A method according to claim 1 wherein Step A comprises intravitreally injecting approximately 300 micrograms of urea in combination with approximately 10 micrograms mitomicyn C per 50 microliters of solution.

15. A method according to claim 1 wherein Step A is repeated a plurality of times and each performance of Step A delivers a dose of 2000 micrograms urea and a dose of 5.0 micrograms of an antimetobolite.

* * * * *